United States Patent [19]
Richelsoph et al.

[11] Patent Number: 6,010,503
[45] Date of Patent: Jan. 4, 2000

[54] LOCKING MECHANISM

[75] Inventors: Marc Evan Richelsoph, Memphis; Kenneth William Russell, Cordova, both of Tenn.

[73] Assignee: Spinal Innovations, LLC, Bartlett, Tenn.

[21] Appl. No.: 09/054,559

[22] Filed: Apr. 3, 1998

[51] Int. Cl.[7] .......................... A61B 17/56; A61B 17/58; A61F 2/30
[52] U.S. Cl. ................................. 606/61; 606/72
[58] Field of Search ................... 606/61, 65, 69, 606/72, 73, 60

[56] References Cited

U.S. PATENT DOCUMENTS

| | | |
|---|---|---|
| 5,443,467 | 8/1995 | Biedermann et al. ............ 606/65 |
| 5,549,608 | 8/1996 | Errico et al. . |
| 5,554,157 | 9/1996 | Errico et al. . |
| 5,586,984 | 12/1996 | Errico et al. . |
| 5,683,392 | 11/1997 | Richelsoph et al. . |

*Primary Examiner*—Michael Buiz
*Assistant Examiner*—Vy Q. Bui
*Attorney, Agent, or Firm*—Kohn & Associates

[57] ABSTRACT

A final fixation assembly includes a rod receiving ring for receiving a portion of a rod therein and including a compressible insert for receiving a portion of the rod therein in a noncompressed condition and conforming allowing the portion of the rod to fixedly lock the portion of the rod therein in a compressed condition. The rod receiving ring maintains the insert in the compressed condition when the insert is seated therein.

23 Claims, 6 Drawing Sheets

Fig-10

LOCKING MECHANISM

TECHNICAL FIELD

The present invention relates to an implant fixation system and locking mechanism. More particularly, the present invention provides a locking mechanism, which can be a multi-planar or fixed mechanism, for securing a rod to an implant.

BACKGROUND OF THE INVENTION

Stabilization of the spine for various conditions, including degenerative disc disease, scoliosis, spondylolithises and spinal stenosis often require attaching implants to the spine and then securing the implants to spinal rods. Such spinal fixation devices can immobilize the vertebrae and can alter the alignment of the spine over a large number of vertebrae by means of connecting at least one elongate rod to the sequence of selected vertebrae. Such rods can span a large number of vertebrae, such as three or four. However, the spine anatomy rarely allows for three or more implants to be directly in line. In order to allow for this irregularity, the rod must be contoured to the coronal plane. With anatomical curvature in the saggital plane found in the lumbar spine, the rod has to be contoured in both planes, requiring considerable effort and surgical time.

For example, the U.S. Pat. No. 5,554,157, issued Sep. 10, 1996, U.S. Pat. No. 5,549,608 issued Aug. 27, 1996, and U.S. Pat. No. 5,586,984 issued Dec. 24, 1996, all to Errico et al. disclose polyaxial locking screws and coupling element devices for use with rod fixation apparatus. The '157 patent discloses a coupling element including an interior axial passage having an interior surface which is inwardly curvate at the lower portion thereof such that it comprises a socket for polyaxially retaining a spherical head of a screw. The coupling element further includes a pair of vertically oriented opposing channels extending down from the top of the coupling element which define therebetween a rod receiving seat. The channel further provides the walls of the upper portion to a pair of upwardly extending members, each including an exterior threading disposed on the upper most portion thereof for receiving a locking nut. During the implantation of the assembly, the locking nut seats against the top of the rod which in turn seats on top of the screw head. The nut causes the rod to be locked between the nut and screw and the screw to be locked in the socket.

The '608 patent discloses a modification wherein a locking ring is disposed about the exterior of the lower portion of the coupling element and provides an inward force on an outwardly tapered portion upon downward translation thereof, causing the interior chamber to crush lock a screw head therein to eliminate the polyaxial nature of the screw element coupling.

The '984 patent discloses a polyaxial orthopedic device including a cutter element having a tapered lower portion including a slotted interior chamber in which a curvate head of a screw is initially polyaxially disposed. The coupling element includes a recess for receiving a rod of the implant apparatus. A locking ring is disposed about the lower portion of the coupling element and provides an inward force on the outwardly tapered portion upon downward translation thereof. The vertical slots are caused to close and crush, thereby locking the screw head within the inter chamber thereof.

With regard to a posterial spinal fixation system, the size of the implant is an important issue. Bulky components can cause soft tissue irritation, as well as comprise the facet joints at the end of a fusion. Minimizing the size of the implants used is critical in spinal surgery with regard to this issue of bulky components. Soft tissue irritation resulting from extensions of implants is a common occurrence. Many times it is caused by the implant being too high relative to its environment. For example, implants can be too high to sufficiently be covered with muscle tissue. Hence, a reduction in the overall height of an implant is a critical advantage for the patient.

Most spine implants utilize a rod connection mechanism that requires a nut, connector, or other component to secure the implant to the rod, such as in those prior art patents discussed above. This connection means has at least some portion that sits above the rod to which the implants are connected. This increases the overall height of the implant assembly in the body.

Several attempts have been made in the prior art to address this concern of the overall height of the implant assembly. Modulok® (manufactured by Zimmer and Wright Medical, Arlington, Tenn.), Versalok® (manufactured by Wright Medical, Arlington, Tenn.), and Paragon® (manufactured by DANEK, Memphis, Tenn.) are all products in the marketplace utilizing a taper connection mechanism to minimize the amount of material situated above the rod in the spinal assembly. However, these types of designs have various inherent difficulties. The Modulok system requires a tapered sleeve to be snapped in place over the rod prior to locking the rod to the implant. The Paragon system requires two tapered sleeves to be used. The Versalok system, specifically designed for lower back fixation, requires that the rod be snapped into a channel and an outer sleeve be brought up to compress the rod interface.

All of the above-mentioned systems have drawbacks, including the bulky instrumentation needed to engage the tapers which somehow must be brought into the surgical environment, thereby causing various difficulties in surgical use. For example, a surgeon usually determines the contour of a rod by contouring the rod and placing it into the saddle or seat of the implants. Then the surgeon examines the contour, removes the rod, and re-contours the rod as required. The Versalok system, due to the design thereof, requires a trialing system for such a procedure. This adds still another step for the surgeon.

In view of the above, it is desirable to have a rod locking mechanism that allows the rod to be readily inserted and removed from the implant, and critically, the mechanism minimizing the height of the implant. This combination of features alleviates the height problem of the prior art while also resolving the issue of multiple contouring steps that are required during the surgical process.

SUMMARY OF THE INVENTION

According to the present invention, there is provided a spinal fixation assembly including rod receiving means for receiving a portion of a rod therein. The assembly further includes a compressible insert for seating the portion of the rod therein in a noncompressed condition and conforming around the portion of the rod to fixedly lock the portion of the rod therein in a compressed condition.

The present invention further provides a method of connecting a spinal fixation assembly to an implant by seating a portion of a rod in a compressible insert and then compressing the insert into a rod receiving member while the compressing insert can form around the portion of the rod, the rod receiving member maintaining the insert in a compressed condition.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE DRAWINGS

Figure 1A:
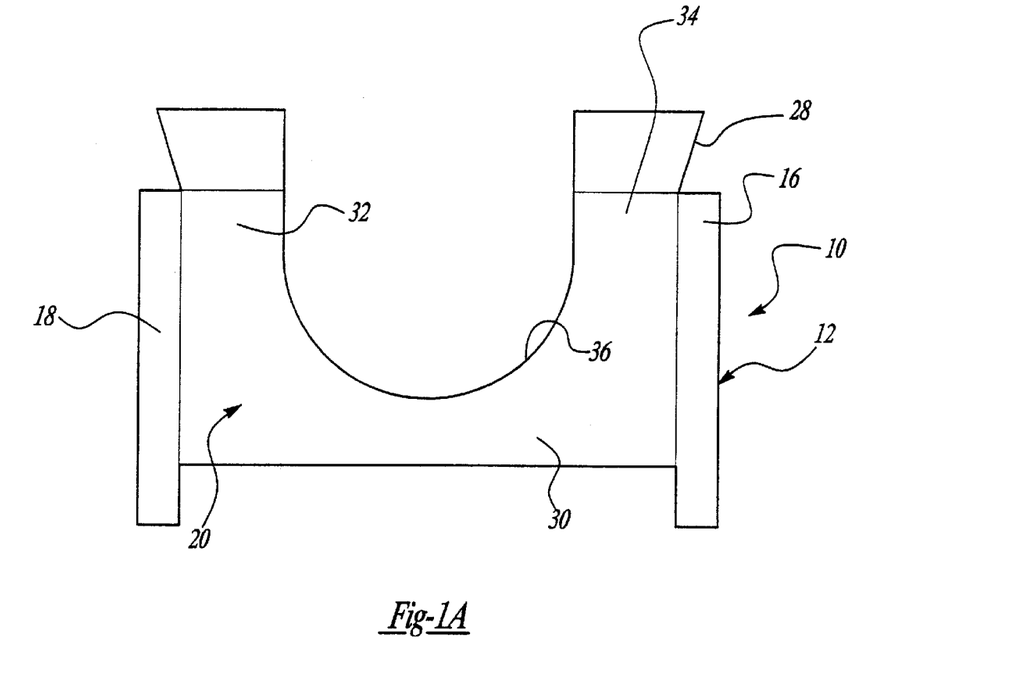
FIGS. 1A and 1B are a schematic illustration of the insert member of the present invention in the unlocked position in FIG. 1A and the locked position in FIG. 1B.
Figure 1B:
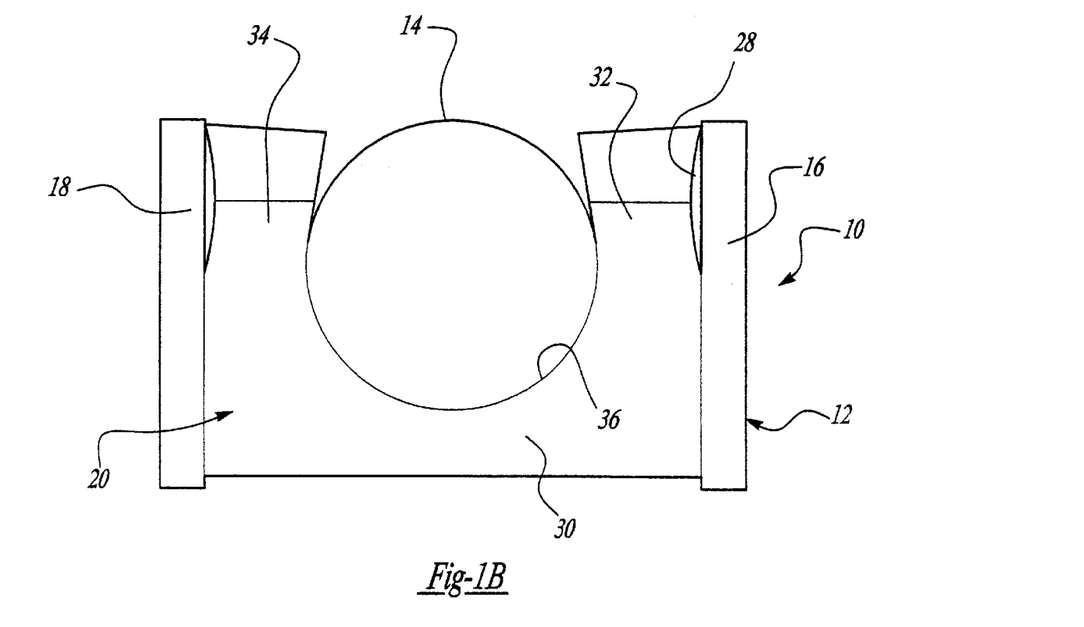

The present invention is most generally shown at 10 in FIGS. 1A and 1B. Most generally, the assembly 10 includes a rod receiving mechanism, generally shown at 12 for receiving a portion of a rod 14 therein. The rod 14 is an elongated rod well known in the art. The present invention is of the type for connecting such a rod, which is usually substantially rigid, relative to a bone member. FIGS. 1A and 1B illustrate the inventive connection of the present invention to the rod 14.

The rod receiving mechanism 12 is shown as two arms 16,18 and will be described in greater detail below. The assembly 10 further includes, most basically, an insert member generally shown at 20 which is a compressible member having a noncompressed condition as shown in FIG. 1A for receiving the rod member 14 therein in a compressed condition as shown in FIG. 1B for fixedly locking the portion of the rod member 14 therein. That is, the insert member 20 is capable of receiving a rod member therein and then being compressed as it is forced actually into the rod receiving member between the arm 16,18 thereby compressing the insert member 20 about the rod 14 seated therein. In this manner, the rod is stripped by the insert member 20 so as to fixedly lock the rod member 14 relative to the assembly 10.

The insert member 20 can be made from many compressible materials well known in the art which are substantially strong enough to withstand sheer and torqueing pressures of the rod 14 during assembly and use of the device 10. The insert 20 must also be sufficiently durable to allow for placement and then replacement of the rod 14 during the initial surgical assembly, as well as during the life of the device as assembled. Examples of such materials are polyethylenes, urethanes, Titanium, Stainless Steel, memory metals, composites, and bioresorbable materials.

Figures 2, 3:
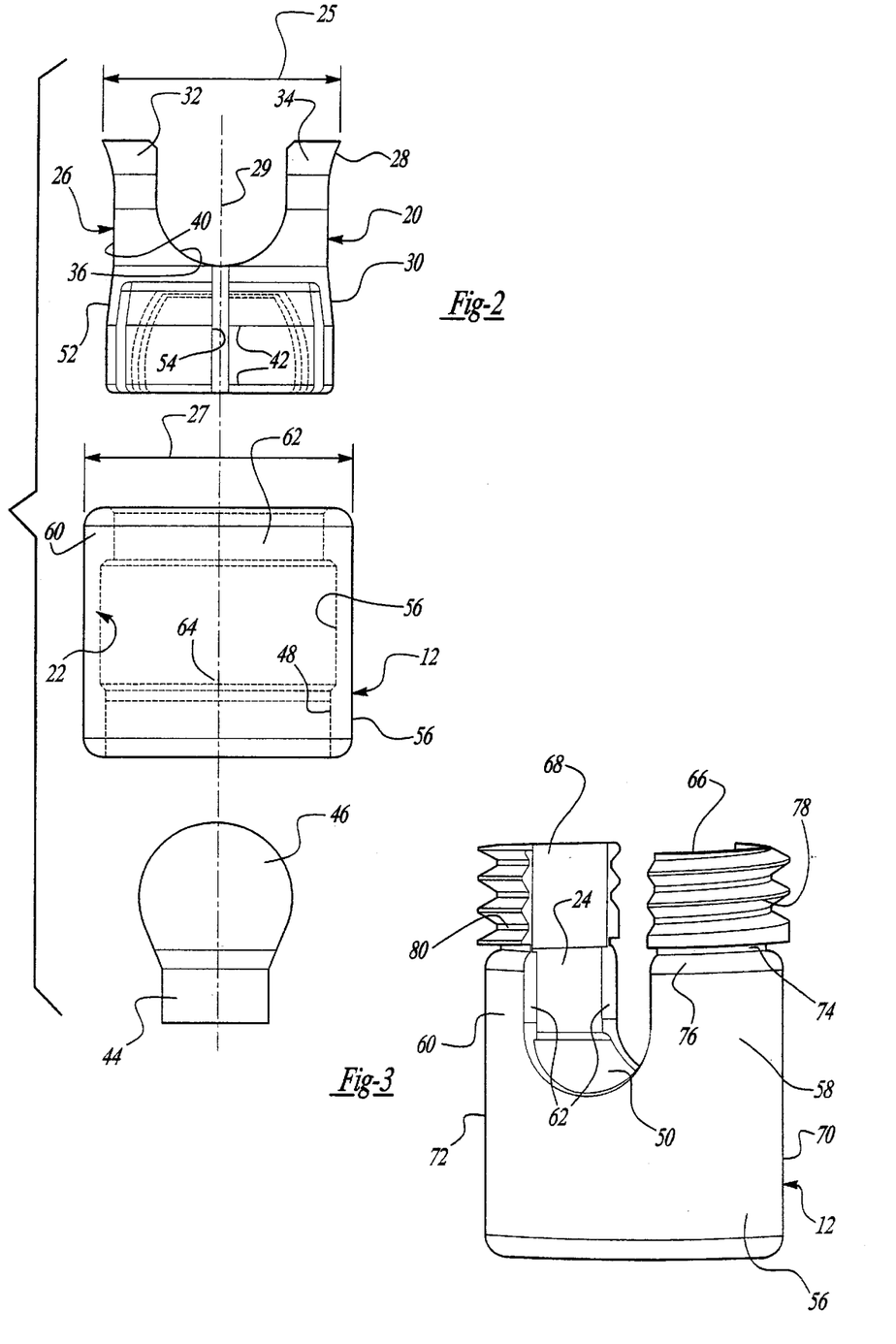
FIG. 2 is an exploded view of a preferred embodiment of the present invention.
FIG. 3 is an enlarged perspective view of the rod receiving ring shown in FIG. 2.

A specific preferred embodiment of the invention is shown in FIG. 2. The rod receiving mechanism includes a substantially ring-shaped member 12, including an inner surface generally shown at 22 defining an insert saddle or seat 24. The insert member generally shown at 20 includes an outer surface generally shown at 26 having at least one compressing portion shown as lip portion 28. Lip portion 28 has a transverse dimension larger than that of the insert seat 24. That is, the diameter taken transaxially across the insert member at one end thereof, along a diameter between opposite sides of the lip portions (shown by hatched lines 25) is greater than the transaxial diameter of the ring member 12, (shown by hatched lines 27), the axis of the ring member being shown by the hatched lines 29 A—A in FIG. 2. Thusly, seating of the insert member 20 within the ring 12 results in compression of the insert member as the lip 28 is forced into the smaller dimension insert seat 24, schematically shown in FIG. 1B. Thusly, the compressible insert member 20 is forced about the rod member 14, as discussed above. Whereas, the insert seat 24 compresses the insert member 20 into the compressed condition when the compressing portion, lip portion 28, is seated within the insert seat 24.

The lip portion 28 can take many configurations, such as beads, a ring, or the like. Preferably, the lip portion 28 allows substantially easy access of the insert member 20 into the insert seat 24. Hence, the outwardly tapering lip portion 28 shown in FIG. 2 is the preferred embodiment. However, this is not to be taken as limiting as other embodiments are possible.

As shown in FIG. 2, the insert member 20 includes a base portion 30 and two arm portions, 32,34. Each of the arm portions 32,34 have an inner surface defining a substantially U-shaped surface 36 for seating the portion of the rod member 14 therein. Each of the arms 32,34 also includes an outer surface 38,40 which includes the outwardly extending lip portion 28 defining the compressing portion of the insert member 20.

In the preferred embodiment shown in FIG. 2, the insert member 20 includes the base portion 30 having a pocket 42 therein for retaining a substantially spherical head portion 46 of a connecting member therein. The connecting member can take the form of a screw member generally shown at 44 having the substantially spherical head portion 46. Such screw members are well known in the art. The inner surface 22 of the rod receiving member 12 includes an inwardly tapering portion 48 which is coaxial with and proximal to the insert seat 24 for seating the base portion 30 therein whereby movement of the base portion 30 of the insert member 20 into the tapering portion 48 of the outer ring 12 compresses the pocket 42 about the head portion 46 seated therein to lock the head portion 46 relative to the assembly 10. In the noncompressed condition, the screw 44 can be pivoted relative to the device 10 allowing for adjustment therebetween.

The inner surface 22 of the rod receiving ring 12 further includes a radially recessed portion 50 disposed between the insert seat 24 and inwardly tapering portion 48. The insert member 20 includes at least one compressible protrusion 52 extending radially outwardly from the base portion 30 for being seated in the recessed portion 50 thereby defining a locking mechanism. The protrusion 52 is engaged by the tapering portion 48 to lock the head portion 46 in the pocket 42 when the insert member 30 is forced from the protrusion 52 being seated in the recessed portion 50 into the tapering portion 48.

As shown in FIG. 2, the insert member 20 is independent of the rod retaining ring 12. A rod 14 can be disposed within the U-shaped seat 36 prior to insertion of the insert member 20 into the rod retaining ring 12 or the insert member 20 can first be substantially disposed within the rod retaining ring 12 and then the rod 14 can be disposed within the U-shaped seat portion 36. Hence, there is great flexibility with regard to when the rod 14 must be locked within the assembly 10.

Likewise, the head portion 46 of the screw member 44 can be disposed in the pocket 42 either prior to disposal of the rod retaining ring member 12 about the insert member 20, or after the base portion 52 is disposed of within the recessed portion 50 of the rod retaining ring 12. In either condition, the pocket 42 of the compressible insert 20 allows for the inner surface of the pocket 42 to sufficiently expand to allow access of the head portion 56 therein. A hinge slot 54 provides even greater flexibility of the pocket 42 to expand to allow insertion of the head portion 46 therein. Once the head portion 46 is disposed within the pocket 42, the rod retaining ring 12 is forced, relative to the insert member 20 such that the protrusion 52 comes in contact with the tapering portion 48 thereby compressing the pocket 42 into frictional engagement with the head portion 46.

The pocket 42 and/or U-shaped seating surface 36 should be a smooth or roughened surface to allow greater frictional contact with the head portion 46 or rod 14, respectively. Likewise, the compressible insert 20 can be made of a material, such as a urethane, polyethylene, or the like, which can have a gripping or substantially "sticky" surface so as to further engage the part disposed therein while providing maximal surface to surface contact.

As shown in FIG. 2, the rod retaining ring includes a base portion 56 and two arm portions 58,60 defining U-shaped recesses 62 for alignment with the U-shaped seating surface 36. The alignment of the surfaces 36,62 allows for total access of the rod 14 through the assembly 10.

The rod retaining ring 12 can also include a key portion 64 extending radially into the tapering portion 48 and recessed portion 50 for engagement with the slot 54 or other slot formed in an outer surface of the base portion 30 to provide an alignment mechanism during the insertion of the insert member 40 into the rod retaining ring 12. Other key and slot configurations also known in the art can be used for providing an alignment mechanism.

FIG. 3 is an enlarged view of the rod receiving ring 12. As shown by the prospective view, the arm portions 58,60 in combination with the base portion 56 defines two coaxial seat portion 62. Each of the arm portions 58,60 include distal portions 66,68 which are relatively distal from the base portion 56. The arm portions 56,58 also include portions 70,72 which are more proximal relative to the base portion 56. There is a weakened intermediate portion 74 in the form of an undercut which smoothly blends through an arcuate portion 76 from the proximal portion 70,72 to the distal portion 66,68. The distal portion 66,68 includes threaded outer surfaces 78,80. The weakened intermediate portion 74 allows separation of the distal portions 66,68 from the proximal portions 70,72 when desired. That is, when sufficient force or torque is applied to the threads 78,80, which is a factor of engaging the threads 78,80 and turning to push the insert member 20 into the assembly, the undercut weakened portion 74 will provide a stress point to allow the threaded arms 66,68 to snap off cleanly. Thusly, the threaded portions 78,80 can be used with a threaded female device for forcing the insert member 20 into the rod retaining member 12 or it can be utilized as an integral part of the assembly to be used with prior art devices such as nuts for retaining a rod member within the seat portion 62. Thusly, the present invention provides a universal rod retaining member which is usable with prior art devices, such as that shown in the co-pending U.S. patent application Ser. No. 08/831,112, filed Apr. 1, 1997 and assigned to the assignees of present invention, or can be used with the compressible insert member 20 of the present invention.

Figures 4, 5:
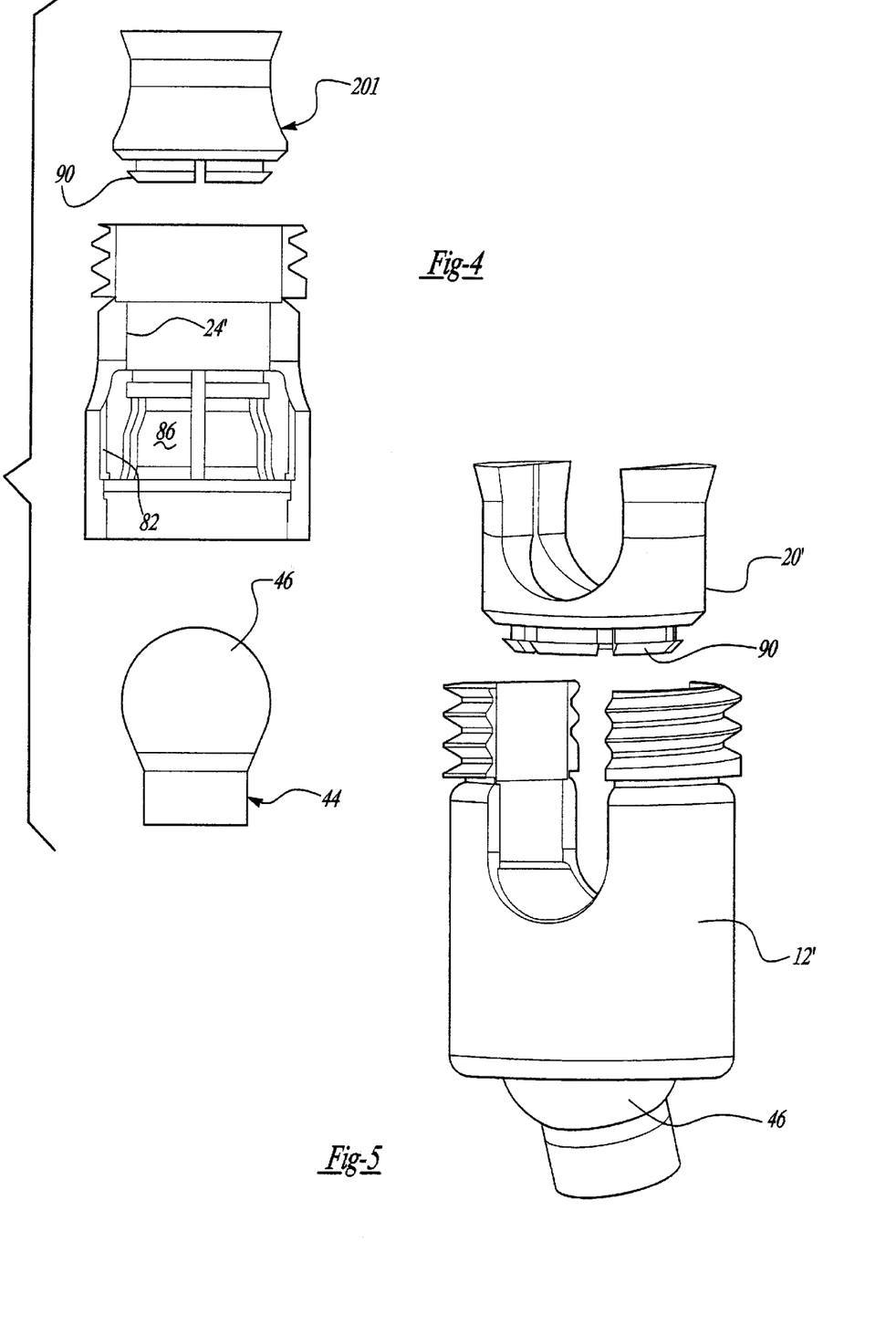
FIG. 4 is an exploded view of a second preferred embodiment of the present invention, partially shown in cross section.
FIG. 5 is an exploded view of the invention as shown in FIG. 4 wherein the screw member is locked relative to the retaining ring of the present invention.

A further embodiment of the present invention is shown in FIG. 4 wherein prime numbers are used to show like structure between the several embodiments. In this embodiment, the rod retaining ring 12' includes a first internally recessed portion 82 retaining therein a screw head retaining insert 84. The screw head retaining insert 84 includes a pocket 86 for receiving and retaining the screw head 46 therein as the insert 84 is forced into the tapering portion 48'. The insert 84 includes an annular groove 88. The insert member 20' includes locking pads 90 which are engageable with the groove 88 such that the disposing of the insert member 20' into the insert seat 24' allows for access and then locking of the locking tabs within the groove 88 thereby forming a substantially integral locking mechanism. This embodiment of the present invention allows for disposition of the screw head 46 into the pocket 86 and locking therein independent of the disposition of the insert 20' and rod 14 which is to be disposed therein.

The insert 84 can be made from various materials well known in the art. Likewise, the inner surface of either the inserts, 84 and/or 20' are made with various polymer materials which are gripping or substantially "sticky" materials to provide maximum surface to surface connection between the parts for more secure engagement therebetween.

Figures 9, 10:
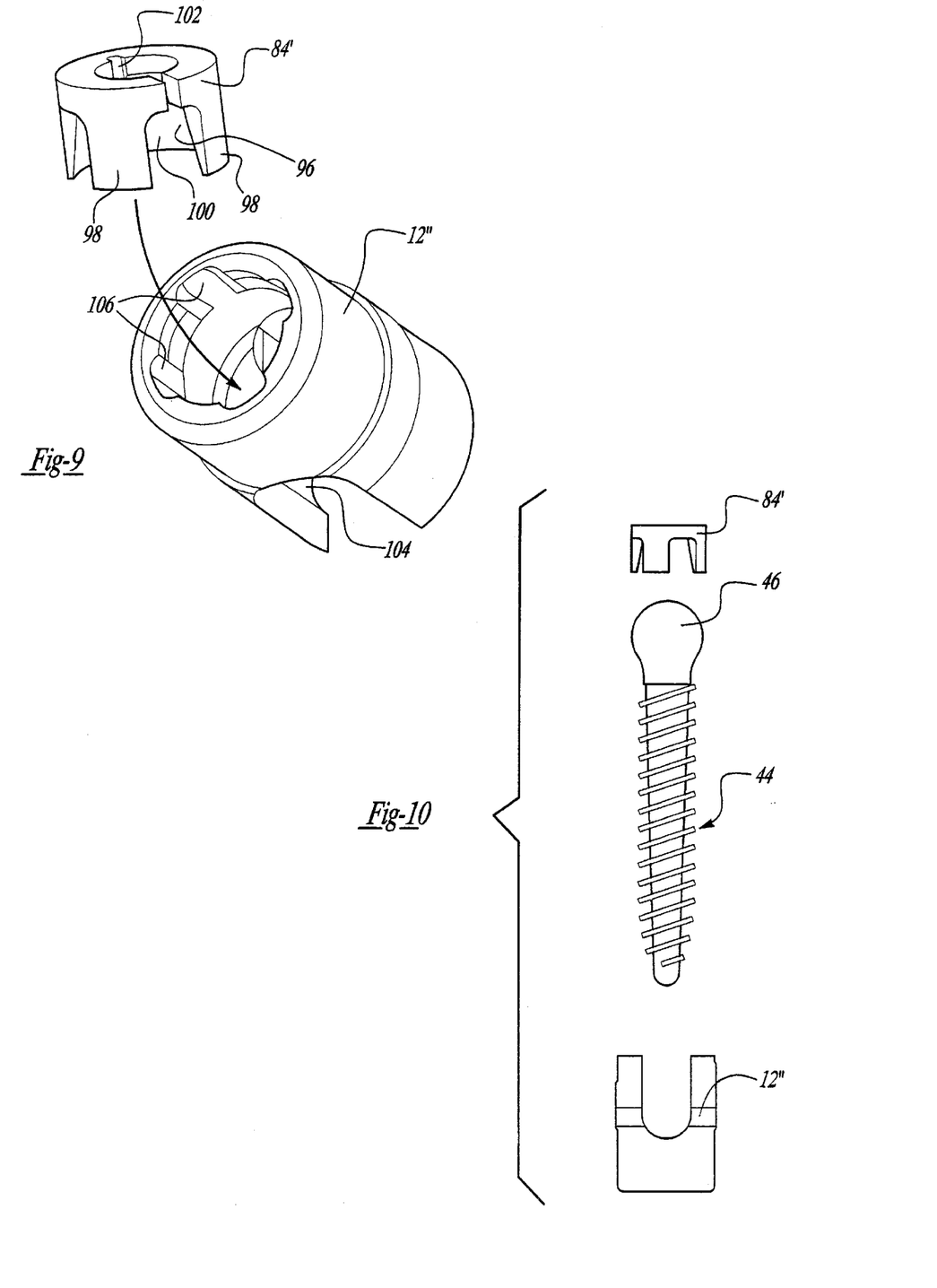
FIG. 9 is a perspective view of a further embodiment of the present invention.
FIG. 10 is an exploded elevational view of the further embodiment in FIG. 9.

The embodiment of the present invention including a retaining ring, a sphere head retaining insert, and an insert member can be further modified as shown in FIGS. 9 and 10. In this embodiment, an implant for locking a screw at any angle includes a screw head retaining insert 84' includes a partially spherical seat 96. The outer wall of the insert 84' is in the form of outwardly tapering tabs 98 having an inwardly tapered inner wall 100. The insert includes a recessed 102 which allows hinging or collapsing of the insert about its diameter. The rod retaining ring 12''' includes a cylindrical opening 104 and a seat for the insert including axially extending slots 106 for receiving the outwardly tapering tabs 98. Thusly, the present invention provides alignment means for aligning the insert relative to its seating position within the ring 12'''. Such alignment can also be used for aligning any of the inserts in any of the embodiments by providing outer tabs mating in predefined slots.

As shown in FIG. 10, the screw 44 is placed into the spherical opening 104 through the body 12''' and the screw retaining insert 84' is inserted from the top over the screw head 46. Locking of the screw occurs with the tapered inner walls 100 of the insert 84' being wedged up against the screw head 46. This can allow for prelocking without the rod or being locked with the rod.

FIG. 5 shows the assembly shown in FIG. 4 wherein the screw head 46 is fixedly locked relative to the rod retaining ring 12'. The insert 20' including tabs 90 is shown in exploded view illustrating the independence of the screw locking mechanism from the rod locking mechanism.

Figures 6, 7, 8:
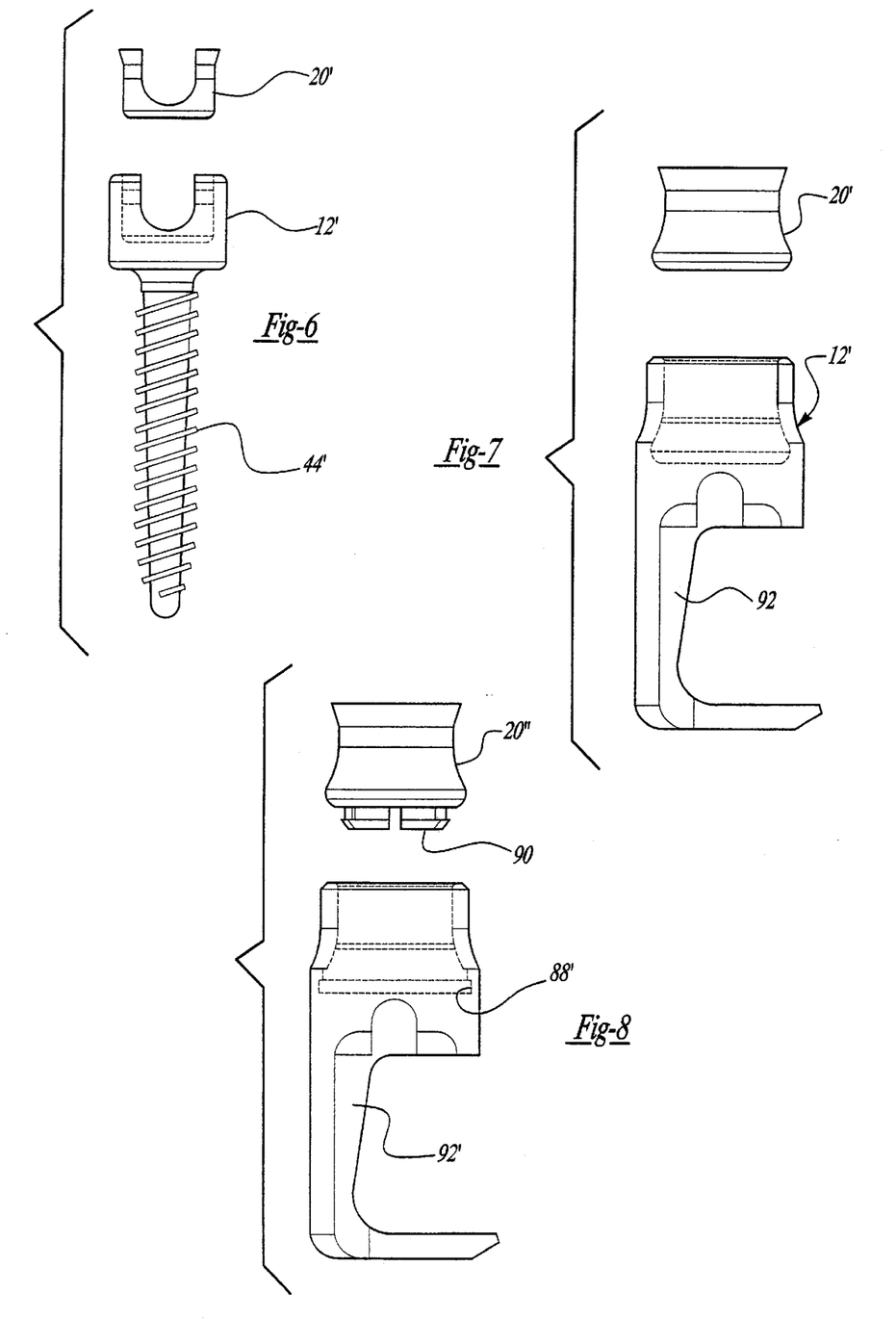
FIG. 6 is a further preferred embodiment of the present invention.
FIG. 7 is a further preferred embodiment of the present invention shown in exploded plan view.
FIG. 8 is a plan exploded view of a further embodiment of the present invention.

FIG. 6 shows a further embodiment in the invention wherein the threaded screw portion 44' is an integral part of the rod retaining ring 12". The insert member shown, 20', can to be the same as that shown in FIG. 5 or as shown in FIG. 1.

FIG. 7 shows a further embodiment of the invention wherein the rod retaining portion 12''' is an integral part of a hook member 92 such as those well known in the art. Again, the insert member 20' can be that chosen from any of the various embodiments. For example, FIG. 8 shows the insert member 20'' including the tabs 90 for engagement in the groove 88' which is shown as an integral part of the base portion of the hook member 92'.

Figures 11, 12:
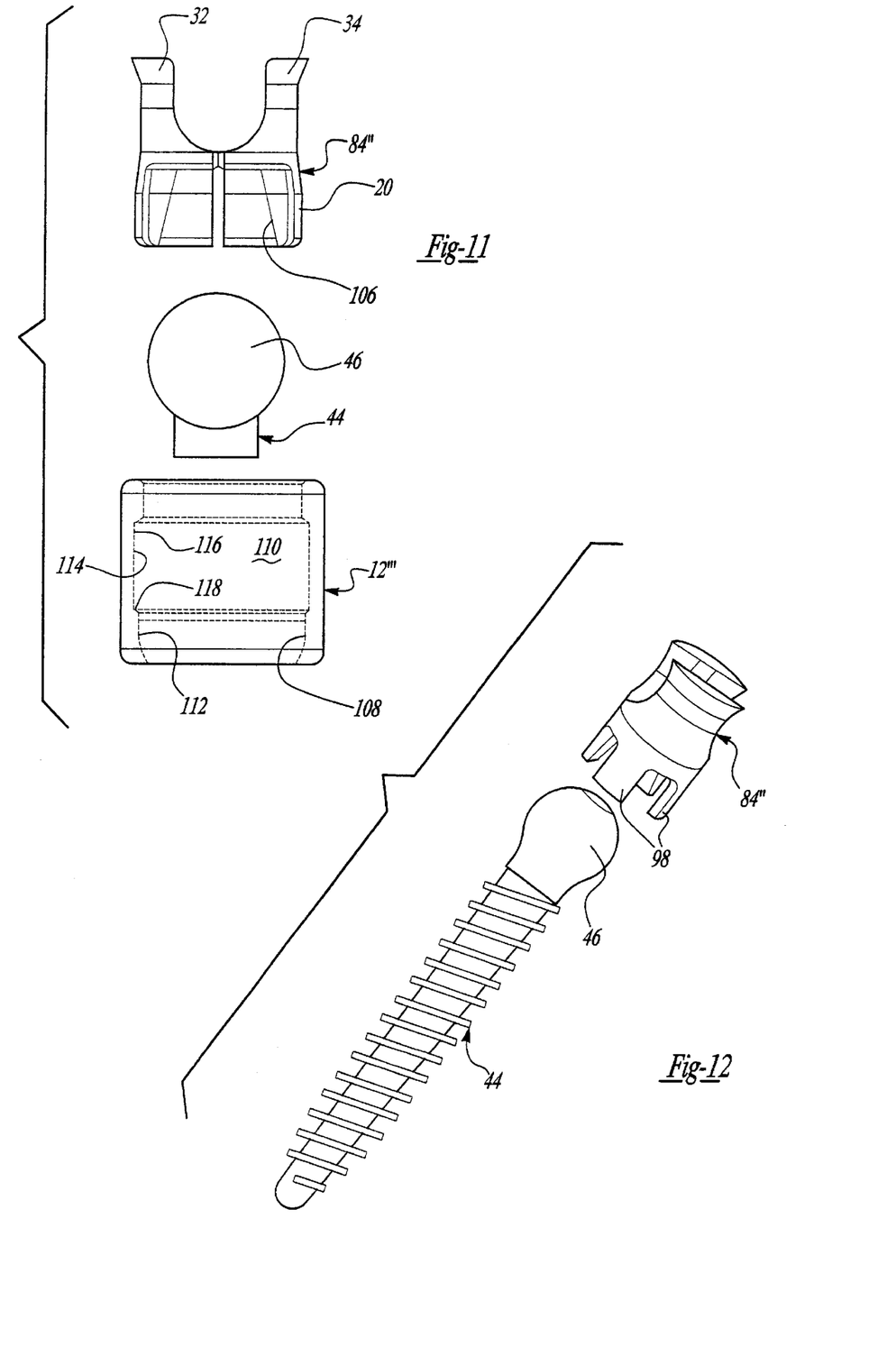
FIG. 11 is an exploded view of a further embodiment of the present invention.
FIG. 12 is an exploded perspective view of the embodiment shown in FIG. 11.

A further embodiment of the invention as shown in FIGS. 11 and 12. This embodiment provides a novel screw head locking mechanism including a first partial seating surface 106 at one end of the insert 84'' and a second partial seating surface 108 in the rod retaining ring 12 4'. The first and second seating surfaces 106,108 lock a screw head 46 therebetween when the insert 84'' is disposed in the compressed condition within the rod retaining ring 12 4' as discussed in further detail below. It is, a single rod retaining ring 12 4' as discussed in further detail below. It is, a single rod retaining ring 12 4' is capable of not only compressing each of the arm portions 32,34 about a rod member 14, but also capable of compressing the partial seat surface 106 against the partial seat surface 108 to lock the screw head 46 therebetween. In this manner, a single act of disposing the insert 84'' within the rod receiving ring 12 4' utilizes a compressing action to both lock the screw head 46 and a rod therein.

More specifically, each of the partial seating surfaces 106,108 are preferentially partially spherical. The rod retaining ring 12 4' includes an axially extending bore therethrough defining passageway 110. The passageway includes an inwardly tapering portion 112 defining the second seating surface 108. The inner passageway 10 also includes a pocket portion 114 which is an outwardly recessed portion of the passageway 110 disposed(?) between ledges 116 and 118, the ledges 116 and 118 retaining the body portion 120 of the insert member 84'' when disposed therebetween. The relative sizing of the body portion 120 and the pocket 114 are such that the body portion 120 is maintained in a compressed condition when disposed within the pocket portion 114. As discussed above, the pocket portion 114 can include further recessed portions which correspond to the outwardly tapering portions 98 of the insert member 84'' for aligning the insert member relative to the retaining ring 12 4'.

In operation, the retaining ring 12 4' is moved up the threaded portion of the screw member 44 while the insert member 84'' is brought down over the screw head 46. The insert member 84'' is then forced into the retaining ring 12 4' either manually, or with a compressing tool which can be in the form of a forked scissor type assembly which would grab the bottom end of the insert member 12 4' about the end of the inwardly tapered portion 112 and another forked arm which would grab against the top of the insert member 84'' adjacent to the ends of the arms 32,34, the compressing scissoring action forcing the insert 84'' into the retaining ring 12 4'. Of course, various other methods and devices can be used to accomplish this result.

In accordance with the present invention, there is thereby provided a general method of connecting the spinal fixation assembly 10 of the present invention, most generally by seating a portion of a rod 14 in a compressible insert 20, 20' and then compressing the insert 20, 20' into a rod receiving member 12, 12', 12'', 12''' while the compressing insert conforms around the rod 14, the rod receiving member 12, 12', 12'', 12''', maintaining the insert 20, 20' in the compressed condition.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A spinal fixation assembly comprising:
rod receiving means for receiving a portion of a rod therein and including compressible insert means for seating the portion of the rod therein in a noncompressed condition and conforming around the portion of the rod to fixedly lock the portion of the rod therein in a compressed condition; said rod receiving means including a U-shaped recess for receiving the portion of the rod therein an inner surface defining an insert seat, said insert means having an outer surface including at least one compressing portion housing a transverse dimension larger than said insert seat, said insert seat compressing said insert means into said compressed condition when said compressing portion is seated within said insert seat; said insert means including a base portion and two arm portions, each of said arm portions having an inner surface defining a substantially U-shaped surface for seating the portion of the rod therein and an outer surface, said outer surface of said arm portions including an outwardly extended lip portion defining said compressing portions.

2. An assembly according to claim 1 wherein said rod receiving means includes insert locking means for locking said insert means within said insert seat.

3. An assembly according to claim 2 wherein said inner surface of said rod receiving means includes a radially recessed portion; said insert means including at least one compressible protrusion extending radially outwardly therefrom for being seated in said recessed portion of said rod receiving means to define said insert locking means.

4. An assembly according to claim 3 wherein said recess is an annular recess.

5. An assembly according to claim 3 wherein said protrusion is an annular protrusion.

6. An assembly according to claim 2 wherein said insert locking means includes a groove adjacent said insert seat, said insert locking means including at least one locking tab adjacent said base of said insert means for locking engagement with said groove when said insert means is fully seated within said insert seat.

7. An assembly according to claim 2 wherein said rod receiving means includes an alignment means for aligning the U-shaped recess of said insert means with said U-shaped recessed of said rod receiving means.

8. An assembly according to claim 7 wherein said inner surface of said rod receiving means includes an axially extending slot, said outer surface of said insert means including a key extending outwardly therefrom for aligning engagement with said slot to define said alignment means.

9. An assembly according to claim 2 wherein said rod receiving means includes a base portion and two arm portions extending therefrom to define a pair of coaxial U-shaped seats for seating the portion of the rod member therein, each of said arm portions including distal portions which are relatively distal from said base portion and proximal portions which are relatively proximal to said base portion, and a weakened intermediate portion allowing separation of said distal portions from said proximal portions where desired.

10. An assembly according to claim 9 wherein said intermediate portion is undercut relative to adjoining portions of said arm and base portions of said rod receiving means for providing a stress point to allow snapping off of said distal portion from said proximal portions upon the application of force thereto.

11. An assembly according to claim 10 wherein each of said distal portions of said rod receiving means includes a threaded outer surface.

12. An assembly according to claim 1 wherein said rod receiving means includes a passageway extending therethrough, said insert seat defining a first end of said passageway, said opposite end of said passageway defining a screw head seat for retaining a substantially spherical screw head therein.

13. An assembly according to claim 1 including an integral screw portion opposite relative to said insert seat.

14. An assembly according to claim 1 wherein said insert means includes said base portion having a pocket therein for retaining a substantially spherical head portion of a connecting member therein, said inner surface of said rod receiving means including an inwardly tapering portion coaxial with and proximal to said insert seat for seating said base portion therein whereby movement of said base portion into said tapering portion compresses said pocket about the head portion seated therein to lock the head portion relative to said assembly.

15. An assembly according to claim 14 wherein said rod receiving means includes insert locking means for locking said insert means within said insert seat.

16. An assembly according to claim 15 wherein said inner surface of said rod receiving means includes a radially recessed portion disposed between said insert seat and said tapering portion, said insert means including at least one compressible protrusion extending radically outwardly from said base portion for being seated in said recessed portion of said rod receiving means to define said insert locking means whereby said protrusion is engaged by said tapering portion to lock the head portion in said pocket when said insert means is forced from said protrusion being seated in said recessed portion into said tapering portion.

17. An assembly according to claim 16 wherein said base portion includes an axially extending hinge slot therethrough for allowing collapsing and expanding of said pocket without compression of said base portion.

18. An assembly according to claim 1 including alignment means for coaxially aligning said rod receiving means and said compressible insert.

19. An assembly according to claim 18 wherein one of said rod receiving means and compressible insert includes at least one slot and the other includes a tab for being aligned within said slot defining said alignment means.

20. An assembly according to claim 1 including screw head locking means including a first partial seating surface in insert means and a second partial seating surface in said rod receiving means, said first and second partial seating surfaces locking a screw head therebetween when said insert is disposed in said compressed condition.

21. An assembly according to claim 20 wherein said first and second partial seating surfaces are each partially spherical.

22. An implant for locking a screw at any angle relative thereto, said implant comprising: a U-shaped insert having at least one compressing portion including a first partial seat portion and a U-shaped body member including a second partial seat portion and compressing means for compressing said first partial seat portion against said second partial seat portion to lock a screw head therebetween; said compressing means including an inner pocket of said body member adjacent to said second partial seat portion, said compressing portion having a transverse dimension larger than said inner pocket, said compressing portion being in a compressed condition and said first partial seat portion being compressed against said second partial seat portion when said insert means is disposed within said pocket.

23. An assembly according to claim 22 wherein said body member comprises a ring including an axially extended bore therethrough defining a passageway, said second partial seat portion including an inwardly tapering portion of said passageway at an end thereof, said ring including an outwardly recessed portion of said passageway proximate to said inwardly tapering portion, said recessed portion including a ledge at each axial end thereof for retaining said insert therebetween.

* * * * *